United States Patent
Cox et al.

(10) Patent No.: US 10,624,835 B2
(45) Date of Patent: Apr. 21, 2020

(54) CLEAR HAIR CONDITIONER COMPOSITION

(71) Applicant: KAO USA INC., Cincinnati, OH (US)

(72) Inventors: Elisabeth Cox, Cincinnati, OH (US); Adam Schrott, Cincinnati, OH (US); Jennifer Deardorff, Cincinnati, OH (US)

(73) Assignee: Kao USA, Inc., Cincinnati, OH (US)

(*) Notice: Subject to any disclaimer, the term of this patent is extended or adjusted under 35 U.S.C. 154(b) by 0 days.

(21) Appl. No.: 15/077,327

(22) Filed: Mar. 22, 2016

(65) Prior Publication Data
US 2017/0273892 A1 Sep. 28, 2017

(51) Int. Cl.
| | |
|---|---|
| *A61K 8/894* | (2006.01) |
| *A61K 8/34* | (2006.01) |
| *A61K 8/81* | (2006.01) |
| *A61K 8/97* | (2017.01) |
| *A61Q 5/00* | (2006.01) |
| *A61Q 5/12* | (2006.01) |

(52) U.S. Cl.
CPC .......... *A61K 8/894* (2013.01); *A61K 8/345* (2013.01); *A61K 8/8152* (2013.01); *A61K 8/97* (2013.01); *A61Q 5/00* (2013.01); *A61Q 5/12* (2013.01); *A61K 2800/262* (2013.01); *A61K 2800/48* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,328,685 A * | 7/1994 | Janchitraponvej | A61K 8/42 424/70.11 |
| 8,420,065 B2 | 4/2013 | Uehara et al. | |
| 8,802,068 B2 | 8/2014 | Knappe et al. | |
| 8,865,145 B2 | 10/2014 | Molenda et al. | |
| 8,932,569 B2 | 1/2015 | Garrison et al. | |
| 2001/0043912 A1 | 11/2001 | Michael | |
| 2003/0165454 A1 | 9/2003 | Snyder et al. | |
| 2006/0079415 A1 | 4/2006 | Kozubal et al. | |
| 2006/0084586 A1 * | 4/2006 | Drzewinski | A61K 8/817 510/119 |
| 2006/0150344 A1 * | 7/2006 | Muller | A61K 8/416 8/405 |
| 2008/0124298 A1 | 5/2008 | Solomon et al. | |
| 2008/0279804 A1 * | 11/2008 | Parker | A61K 8/25 424/70.11 |

FOREIGN PATENT DOCUMENTS

| | | |
|---|---|---|
| DE | 199 50 711 A1 | 5/2001 |
| DE | 102011083310 A1 | 3/2013 |
| WO | WO 94/18934 A1 | 9/1994 |

OTHER PUBLICATIONS

Chaney, P., "The Secret to Hair Care in the Personal Care Industry: Gaur Gum," Economy Polymers Blog, Jun. 24, 2014, downloaded from http://www.economypolymers.com/blog/the-secret-to-hair-care-in-the-personal-care-industry-guar-gum, accessed Feb. 25, 2016, 1 pg.
Chemical Substance—Polyquaternium-37, Health Canada, Drug and Health Products, accessed Feb. 25, 2016 from http://webprod.hc-sc.gc.ca/nhpid-bdipsn/ingredReq.do?id=12234&lang=eng, 1 pg.
Polyquaternium-52 Cosmetic Ingredient (INCI), SpecialChem, accessed Feb. 25, 2016 from http://cosmetics.specialchem.com/inci/polyquaternium52, 1 pg.
Polyquaternium, Wikipedia, the free encyclopedia, Dec. 8, 2015, accessed Feb. 25, 2016 from https://en.wikipedia.org/w/index.php?title=Polyquaternium&printable=yes, 4 pgs.
Silicone Polyols, Main Literature Page, Genesee Polymers Corporation, accessed Feb. 25, 2016 from http://www.gpcsilicones.com/polyols.html, 4 pgs.
International Search Report and Written Opinion dated May 23, 2017 for Application No. PCT/US2017/021050, 10 pgs.
European Examination Report dated Nov. 27, 2019 for Application No. EP 17711540.9, 5 pgs.

* cited by examiner

*Primary Examiner* — David J Blanchard
*Assistant Examiner* — Sarah J Chickos
(74) *Attorney, Agent, or Firm* — Frost Brown Todd LLC

(57) ABSTRACT

A hair conditioner which provides hair conditioning, detangling, frizz control and reduced flyaway benefits, without weighing down hair or loosing hair volume, in a clear composition, is disclosed. The composition utilizes a combination of high levels of PEG/PPG silicone surfactants together with cationic polymeric thickeners (such as polyquaternium-37) to provide those benefits.

16 Claims, No Drawings

CLEAR HAIR CONDITIONER COMPOSITION

TECHNICAL FIELD

The present invention relates to hair conditioner compositions and the hair conditioning benefits that can be obtained from such compositions.

BACKGROUND OF THE INVENTION

The hair conditioner compositions of the present invention provide hair conditioning, de-tangling, frizz control, and reduced flyaways without weighing down the hair. These benefits can now be obtained in a visually clear composition. The latter aspect of the present invention is a particular aesthetic benefit in view of the fact that many hair conditioners are opaque suspensions. Opaque suspensions are often associated with increased conditioning since conditioning agents are more freely available to attach to the hair. It is unusual for these hair conditioning benefits to be obtained without weighing the hair down, making the hair feel heavy or greasy or reducing hair volume. In contrast, these benefits are obtained herein using a combination of high levels of PEG/PPG silicone surfactants together with a cationic polymeric thickener. Thus, the hair conditioning benefits are provided without requiring use of traditional conditioning ingredients. The high level of PEG/PPG silicone surfactant permits the unexpected dispersal of the cationic polymeric thickener, which is important in providing a clear composition.

Currently hair conditioning technologies utilize emulsions containing:

1. fatty alcohols for feel and formulation consistency and viscosity (e.g., lauryl, myristyl, cetyl, stearyl, behenyl alcohols);
2. alkyl quaternary ammonium compounds to act as emulsifiers and detangling agents (e.g., cetrimonium chloride, steartrimonium chloride, behentrimonium chloride, behentrimonium methosulfate, quaternium-91, dicetyl dimonium chloride, distearyldimonium chloride); and
3. oil agents to increase conditioning—these are materials which are either not soluble or not dispersible in water (e.g., vegetable-derived triglycerides, animal-derived triglycerides, mineral oils, esters, ethers, silicone oils, such as dimethicone or amodimethicone).

These emulsions and materials contribute conditioning and detangling benefits to the hair, but also weigh it down and make the hair feel heavy or greasy when dry. The present invention offers the benefits of conditioning, detangling, fizz control, and reduced flyaways, without weighing the hair down, making the hair feel heavy or greasy, or reducing hair volume.

U.S. Published Patent Application 2008/0124298, Hoffmann et al., published May 29, 2008, describes a conditioner composition which provides shine to hair. The composition is formulated using synthetic mica coated with a metal oxide material. The disclosed composition can optionally include PEG/PPG dimethicone as an emulsifier and a cationic polyquaternary polymer to hold hair in place.

U.S. Published Patent Application 2012/0251473, Knappe et al., published Oct. 4, 2012, describes a composition for treating hair which includes a cosmetic carrier, at least one cyclic siloxane, at least one $C_8$-$C_{30}$ alkyl PEG/PPG dimethicone, and at least one cationic protein hydrolysate.

U.S. Published Patent Application 2011/0293551, Molenda et al., published Dec. 1, 2011, defines a leave-in hair conditioner in the form of a water-in-oil emulsion which comprises an oil component, a silicone surfactant (which can be PEG/PPG dimethicone), an alkoxylated hydroxylated amino silicone, and water.

U.S. Published Patent Application 2011/0110992, Garrison et al., published May 12, 2011, defines a composition for reducing hair frizziness which comprises a particulate surface-modified aluminum hydroxide material, together with a hydrophobic film former. The composition may include PEG/PPG dimethicones as a water-in-silicone emulsifier and also may optionally include polyquaternium materials.

BRIEF SUMMARY

The present application defines a hair conditioner composition which comprises:

(A) from about 3% to about 15% of at least one polyoxyethylene/polyoxypropylene-derived silicone surfactant; and (B) a cationic polymer thickener;

wherein the weight ratio of (A) to (B) is greater than about 4:1.

The present application also describes a method of treating hair comprising adding to the hair an effective amount of an aqueous cosmetic composition which comprises:

(A) from about 3% to about 15% of at least one polyoxyethylene/polyoxypropylene-derived silicone surfactant; and (B) a cationic polymer thickener;

wherein the weight percent ratio of (A) to (B) is greater than about 4:1.

As used herein, all percentages and ratios are "by weight," unless otherwise specified. Further, all published documents referred to in this application are incorporated by reference herein in their entirety.

DETAILED DESCRIPTION

The hair conditioners of the present invention are generally formulated as rinse-off conditioners. They utilize high levels of PEG/PPG silicone surfactants together with cationic polymeric thickeners to provide hair conditioning, de-tangling, frizz control, and reduced flyaway hair benefits, in a clear hair conditioner composition, without weighing down hair, reducing hair volume, or providing undesirable greasy hair. The components of the present invention will be discussed in detail below.

The invention includes relatively high levels of at least one polyoxyethylene (PEG)/polyoxypropylene (PPG) silicone surfactant. For example, this component can be present at a level of from about 3% to about 15%, such as from about 3% to about 10%, by weight, of the conditioner composition. In one embodiment, the silicone surfactant defined has a cloud point of greater than about 25° C. and less than about 90° C., at 4% in water. The silicone surfactants utilized in the present invention can be symbolized by the formula PEG/PPG X/Y dimethicone, wherein X is an integer greater than 0 (such as from about 2 to about 30), and Y is an integer from 0 to 30 (such as from about 2 to about 30).

Examples of silicone surfactants which can be used in the present invention include: PEG/PPG-14/4 dimethicone; PEG/PPG-4/12 dimethicone; PEG/PPG-23/6 dimethicone; PEG/PPG-20/23 dimethicone; PEG-12 dimethicone and PEG-8 dimethicone. Examples of other silicone surfactants that may be used in the present invention include: PEG/PPG-3/10 dimethicone; PEG/PPG-4/12 dimethicone; PEG/PPG-6/4 dimethicone; PEG/PPG-6/11 dimethicone; PEG/

PPG-8/14 dimethicone; PEG/PPG-8/26 dimethicone; PEG/PPG-10/2 dimethicone; PEG/PPG-12/16 dimethicone; PEG/PPG-12/18 dimethicone; PEG/PPG-14/4 dimethicone; PEG/PPG-15/5 dimethicone; PEG/PPG-15/15 dimethicone; PEG/PPG-16/2 dimethicone; PEG/PPG-16/8 dimethicone; PEG/PPG-17/18 dimethicone; PEG/PPG-18/6 dimethicone; PEG/PPG-18/12 dimethicone; PEG/PPG-18/18 dimethicone; PEG/PPG-19/19 dimethicone; PEG/PPG-20/6 dimethicone; PEG/PPG-20/15 dimethicone; PEG/PPG-20/20 dimethicone; PEG/PPG-20/23 dimethicone; PEG/PPG-20/29 dimethicone; PEG/PPG-22/23 dimethicone; PEG/PPG-22/24 dimethicone; PEG/PPG-23/6 dimethicone; PEG/PPG-25/25 dimethicone; PEG/PPG-27/27 dimethicone; PEG/PPG-30/10 dimethicone; and mixtures thereof.

Such silicone surfactants are well-known in the art and are commercially-available from, for example, Dow Corning, Midland, Mich., and Grant Industries, Elmwood Park, N.J.

The compositions of the present invention also include at least one cationic polymeric thickener, frequently at a level from about 0.2 to about 2% of the conditioner composition, for example, from about 0.5% to about 1.2% of the composition. The weight ratio of (A) (silicone surfactant) to (B) (cationic polymeric thickener) in the compositions of the present invention is greater than about 4:1, for example, greater than about 5:1. Examples of cationic polymeric thickening materials utilizing the present invention are polyquaternium materials, such as polyquaternium-37, polyquaternium-52, and mixtures of those materials.

Examples of cationic polymeric thickener materials which can be utilized in the compositions of the present invention include poly (methacryloyloxyethyltrimethylammonium chloride) (polyquaternium-37), and/or quaternized cellulose derivatives (polyquaternium-10), and/or cationic alkylpolyglycosides, and/or cationized honey, and/or cationic guar derivatives, and/or polymeric dimethyldiallylammonium salts and copolymers thereof with esters and amids of acrylic acid and methacrylic acid, and/or copolymers of vinylpyrrolidone with quaternized derivatives of dialkylaminoalkyl acrylate and methacrylate and/or vinylpyrrolidone-vinylimidazoinlium methylchloride copolymers, and/or quaternized polyvinyl alcohol, and/or polyquaternium-2, and/or polyquaternium-7, and/or polyquaternium-16, and/or polyquaternium-17, and/or polyquaternium-18, and/or polyquaternium-24, and/or polyquaternium-27. Polyquaternium materials are preferred, with polyquaterium-37 and polyquaternium-52 being particularly preferred.

The conditioner compositions of the present invention can be formulated using standard conditioner components, together with the required components defined above. The amount of oily materials utilized is generally kept low since one of the benefits of the present invention is that conditioner compositions can be formulated to provide effective results without imparting a great deal of oily materials to the hair. For example, the total amount of oily materials in the composition (e.g., fatty alcohols, alkyl quaternary ammonium compounds, and oil agents) is less than about 5% of the composition, preferably less than about 2% of the composition. The hair conditioner compositions of the present invention are preferably formulated as clear compositions, the compositions can have a viscosity of at least about 5,000 centipoise, and a percent transmittance value above 70%, for example, above 80%. Water can be the primary solvent of the compositions of the present invention. For example, such compositions can include at least about 70% water, for example at least about 80% water, or at least about 90% water.

The compositions of the present invention can optionally include volatile cyclomethicones, well-known in the hair conditioner art, as well as non-volatile silicones, such as arylated silicones, such as phenyltrimethicone or dimethiconol. In addition, naturals oils, such as olive oil, almond oil, avocado oil, jojoba oil, coconut oil, palm oil, sunflower oil, peach kernel oil, wheat germ oil, night primrose oil, or soya oil, or their mixtures, can also be included. Concentrations of such oily materials are generally below about 2%, preferably below about 1%, such as below about 0.5%, in order to keep the compositions from leaving a significant oily residue on the hair. Other compositions of the present invention can optionally include fatty acid esters, such as isopropyl myristate, isopropyl palmitate, isopropyl stearate and isopropyl isostearate, oleyl oleate, isocetyl stearate, hexyl laurate, dibutyl adipate, dioctyl adipate, myristyl myristate, oleyl erucate, cetyl palmitate, and mixtures thereof. Cationic surfactants, such as cetyl trimethyl ammonium chloride, and behentrimonium chloride, can also be included. If utilized, all of these materials are utilized at low levels. Natural plant extracts can also be included at their art-established hair conditioner levels. Nonionic polymers, such as polyvinyl pyrrolidone, can also be included in the compositions of the present invention.

The pH of the compositions of the present invention vary from about 3 to about 7, such as from about 4.5 to about 6. The pH of the compositions can be adjusted using organic acids, such as citric acid, lactic acid, malic acid and succinic acid; or alkaline materials, such as sodium hydroxide or potassium hydroxide.

Glyceryl esters, at levels of from about 3.5% to about 10% of the composition, such as esters of coconut fatty acid, palm kernel fatty acid, palm oil fatty acid, lauric acid, myristic acid, caprylic acid, capric acid, and oleic acid, can be included. Polyethylene or polypropylene glycol can be included at from about 0.3% to about 2% of the composition. Glycerin can be included at from about 1% to about 20% of the composition.

Fragrances, chelating agents, preservatives, colorants and other conventional cosmetic ingredients can also be included at their usual concentrations for use in hair conditioner compositions.

Nonionic surfactants, such as sorbitan esters, $C_{10}$-$C_{22}$ fatty alcohol alkoxylates and alkyl polyglucocides can also be included, at their art-established usage levels.

Compositions of the present invention can also optionally comprise conventionally-utilized UV filters either for stabilization of the product color or for protection of hair from environmental influences, such as loss of elasticity or loss of hair color (or both). The compositions of the present invention can also optionally include hair restructuring agents, such as ceramide compounds, fatty acids and phytosterols, or their mixtures.

The hair conditioning compositions of the present invention are used in the conventional way that a hair conditioner is used. Specifically, an effective amount of the hair conditioner is worked into the hair (preferably shampooed hair), and is allowed to remain in the hair for a short period of time (e.g., between about 30 seconds and about 2 minutes). The composition may be left in the hair, but generally is rinsed out of the hair with water, thereby providing the hair conditioning benefits of the present invention. By "effective amount of conditioner," as used herein, is meant a portion of hair conditioner of approximately 5 to about 20 milliliters, which is applied to and worked into the wet hair.

EXAMPLES

Compositions of the present invention, having the formulations set forth in the following table, are made as described:

| | Example | 1 | 2 | 3 | 4 | 5 | 6 | 7 | 8 |
|---|---|---|---|---|---|---|---|---|---|
| A (RT) | Deionized water | Balance | Balance | Balance | Balance | Balance | Balance | Balance | Balance |
| | Citric Acid (or other acid suitable to QS pH) | QS | QS | QS | QS | QS | QS | QS | QS |
| | Propylene Glycol | | | 1 | 1.5 | | | | |
| | Glycerin | 7.50 | 2.5 | | | 10 | 15 | | |
| B (RT Premix) | PEG/PEG-14/4 dimethicone | 3.5 | | | | | | 3.5 | |
| | PEG/PEG-4/12 dimethicone | | 5 | | | | | | |
| | PEG/PPG-23/6 dimethicone | | | 6.5 | | | | | 2.5 |
| | PEG/PPG-20/23 dimethicone | | | | 5 | | | | 2.5 |
| | PEG-12 dimethicone | | | | | 5 | | | |
| | PEG-8 dimethicone | | | | | | 10 | 1.5 | |
| | Polyquaternium-37 | 0.65 | 0.75 | 1 | 1.1 | 0.5 | 0.5 | 0.6 | 0.6 |
| C (RT) | Fragrance | QS | QS | QS | QS | QS | QS | QS | QS |
| | Polysorbate-20 | 0.25 | 0.25 | | | | | 0.25 | 0.25 |
| | PEG-40 Hydrogenated Castor Oil | | | 0.5 | 0.5 | 0.5 | 0.5 | | |
| | Preservative | QS | QS | QS | QS | QS | QS | QS | QS |

The compositions are made in a conventional manner as follows: in a vessel suitable for the complete batch, add phase A ingredients individually with mixing in between to ensure homogeneity. In a separate vessel, prepare phase B by dispersing polyquaternium-37 in dimethicone copolyol. Once dispersed, add phase A and mix until homogeneous. Next, add the phase C ingredients individually with mixing to the mixed phase AB. Ensure adequate mixing throughout, to be conducted at room temperature or under gentle heat, if needed.

These exemplary compositions are applied, in an effective amount, to condition hair, as described above.

What is claimed is:

1. A clear hair conditioner comprising:
   (A) from about 3% to about 15% of at least one polyoxyethylene/polyoxypropylene-derived silicone surfactant; and
   (B) a cationic polymer thickener;
   wherein the weight ratio of (A) to (B) is greater than about 4:1 and wherein the cationic polymer thickener is selected from the group consisting of polyquaternium-52, polyquaternium-37 and mixtures thereof.

2. The conditioner according to claim 1, wherein the at least one polyoxyethylene/polyoxypropylene-derived silicone surfactant has a cloud point greater than about 25° C., but less than about 90° C., at 4% in water.

3. The conditioner according to claim 2, wherein said at least one polyoxyethylene/polyoxypropylene-derived silicone surfactant is of the type PEG/PPG-X/Y dimethicone.

4. The conditioner according to claim 3, wherein X is an integer greater than 0, and Y is an integer from 0 to about 30.

5. The conditioner according to claim 1, which additionally comprises glyceryl ester, polyethylene, or polypropylene glycol, and mixtures thereof.

6. The conditioner according to claim 5, wherein the glyceryl ester is selected from the group consisting of esters of coconut fatty acids, palm kernel fatty acid, palm oil fatty acid, lauric acid, myristic acid, caprylic acid, capric acid, oleic acid, and mixtures thereof.

7. The conditioner according to claim 1, wherein the weight ratio of (A) to (B) is greater than about 5:1.

8. The conditioner according to claim 1 which additionally comprises glycerin.

9. The conditioner according to claim 1 which additionally comprises greater than about 80% by weight water.

10. The conditioner according to claim 1, wherein the total amount of (A) at least one polyoxyethylene/polyoxypropylene-derived silicone surfactant, (B) the cationic polymer thickener, and water is greater than 90% by weight of the conditioner composition.

11. The conditioner according to claim 10, having a viscosity greater than about 5,000 centipoise.

12. A method of treating hair comprising adding to the hair, which has been wetted, an effective amount of a clear aqueous cosmetic hair conditioner composition comprising:
   (A) from about 3% to about 15% of at least one polyoxyethylene/polyoxypropylene-derived silicone surfactant; and
   (B) a cationic polymer thickener;
   wherein the weight ratio of (A) to (B) is greater than about 4:1 and wherein the cationic polymer thickener is selected from the group consisting of polyquaternium-52, polyquaternium-37, and mixtures thereof.

13. The method of treating hair according to claim 12 which additionally comprises the step of rinsing the conditioner composition out of the hair with water.

14. The method of treating hair according to claim 12, wherein the at least one polyoxyethylene/polyoxypropylene-derived silicone surfactant is of the type PEG/PPG-X/Y dimethicone.

15. The method of treating hair according to claim 14, wherein X is greater than 0, and Y is an integer from 0 to about 30.

16. A clear aqueous hair conditioner consisting essentially of:

(A) from about 3% to about 15% of at least one polyoxyethylene/polyoxypropylene-derived silicone surfactant;
(B) polyquaternium-37;
(C) polypropylene glycol; and
(D) glycerin;

wherein the weight ratio of (A) to (B) is greater than about 4:1.

\* \* \* \* \*